United States Patent
Aljefri

(10) Patent No.: US 11,534,092 B2
(45) Date of Patent: Dec. 27, 2022

(54) BLOOD COLLECTION TUBE

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Ahmad Mohammed Shikan Aljefri, Jeddah (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 946 days.

(21) Appl. No.: 16/364,504

(22) Filed: Mar. 26, 2019

(65) Prior Publication Data

US 2020/0305781 A1     Oct. 1, 2020

(51) Int. Cl.
 *A61B 5/15* (2006.01)
 *B04B 5/04* (2006.01)
 *A61J 1/20* (2006.01)

(52) U.S. Cl.
 CPC .. *A61B 5/150755* (2013.01); *A61B 5/150099* (2013.01); *A61B 5/150343* (2013.01); *A61B 5/150351* (2013.01); *A61J 1/202* (2015.05); *B04B 5/0428* (2013.01)

(58) Field of Classification Search
 CPC ........ A61B 5/150755; A61B 5/150099; A61B 5/150343; A61B 5/150351; A61B 5/15003; A61B 5/154; A61J 1/202; B04B 5/0428; B01L 2300/123; B01L 2400/0481; B01L 3/5021
 See application file for complete search history.

(56) References Cited

U.S. PATENT DOCUMENTS

| | | | |
|---|---|---|---|
| 2,460,641 A | | 2/1949 | Kleiner |
| 3,181,529 A | * | 5/1965 | Wilburn ............ A61B 10/0045 600/580 |
| 3,750,645 A | | 8/1973 | Bennett et al. |
| 3,965,889 A | | 6/1976 | Sachs |
| 4,187,861 A | | 2/1980 | Heffernan |
| 4,867,172 A | | 9/1989 | Haber et al. |

(Continued)

FOREIGN PATENT DOCUMENTS

| | | | | |
|---|---|---|---|---|
| JP | 07051253 A | * | 2/1995 | ......... A61B 5/15003 |
| WO | WO-2008119739 A1 | * | 10/2008 | ............ B01L 3/502 |
| WO | WO-2013145901 A1 | * | 10/2013 | ............ B01L 3/502 |

*Primary Examiner* — Sean P Dougherty
(74) *Attorney, Agent, or Firm* — Oblon, McClelland, Maier & Neustadt, L.L.P.

(57) ABSTRACT

A blood collection tube for physically separating the plasma and red blood cell fractions of a centrifuged sample is described. The blood collection tube has an elastomeric sleeve with rigid tube segments at both ends. Following blood collection and centrifugation, the elastomeric sleeve may be twisted to constrict its inner diameter and physically separate the two fractions. The blood collection tube may be secured in this position with a pin and a clamp, and further with an adhesive tape with pH paper. This enables blood samples to be transferred over long distances to a central lab facility without spoiling.

20 Claims, 9 Drawing Sheets

(56) References Cited

U.S. PATENT DOCUMENTS

| | | | |
|---|---|---|---|
| 5,632,396 A * | 5/1997 | Burns | A61B 5/150732 |
| | | | 220/254.1 |
| 9,370,327 B2 | 6/2016 | Teoh | |
| 9,623,410 B2 * | 4/2017 | Ohashi | B01L 3/502 |
| 9,945,839 B2 | 4/2018 | Campton et al. | |
| 2003/0036731 A1 | 2/2003 | Wilkinson et al. | |
| 2004/0162540 A1 * | 8/2004 | Walenciak | A61B 5/150473 |
| | | | 604/411 |
| 2009/0269246 A1 * | 10/2009 | Hasegawa | B65D 51/222 |
| | | | 422/400 |
| 2010/0303688 A1 * | 12/2010 | Andersen | A01N 1/02 |
| | | | 422/549 |
| 2014/0124446 A1 * | 5/2014 | Ohashi | G01N 30/6052 |
| | | | 210/656 |

* cited by examiner

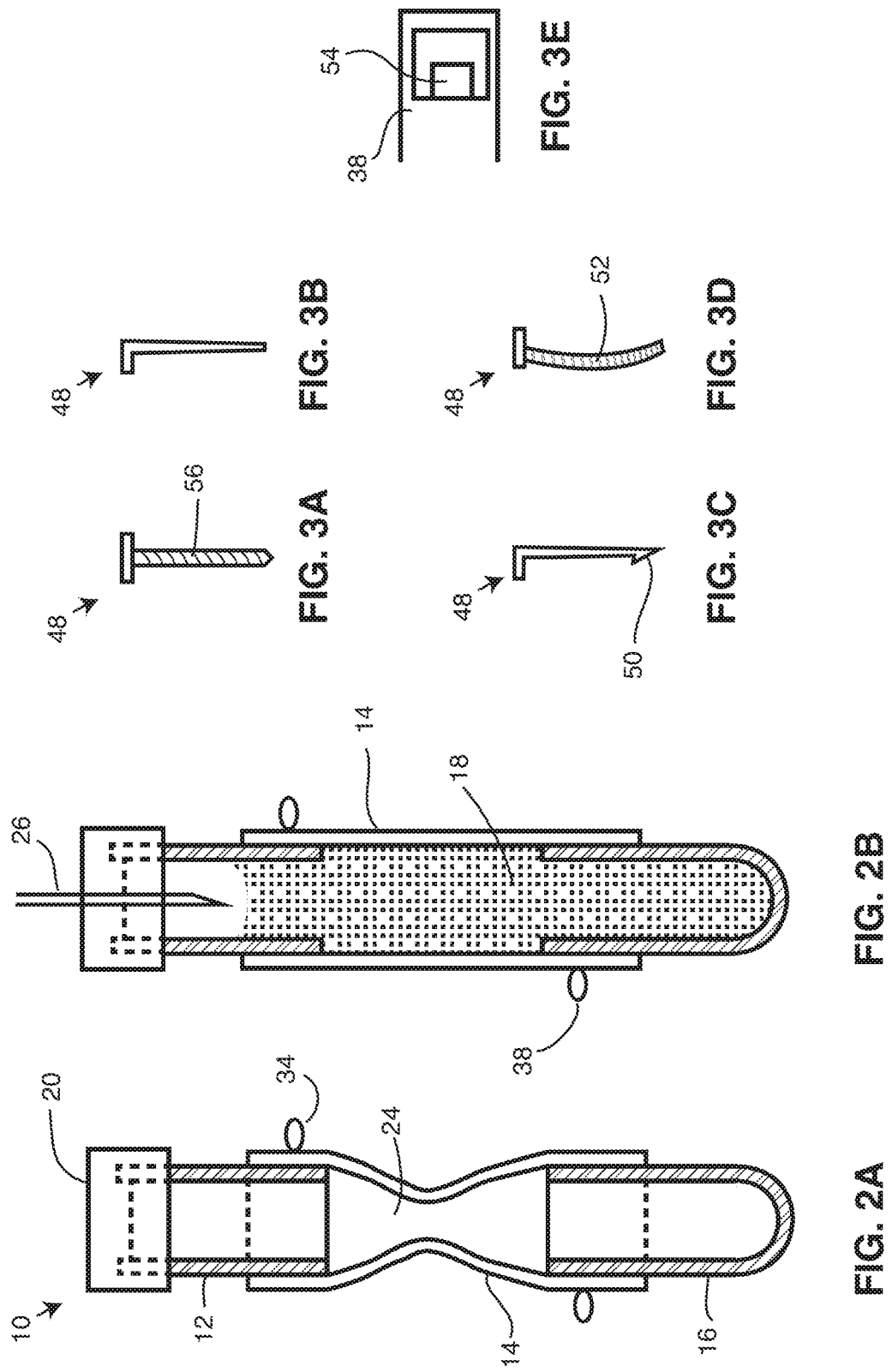

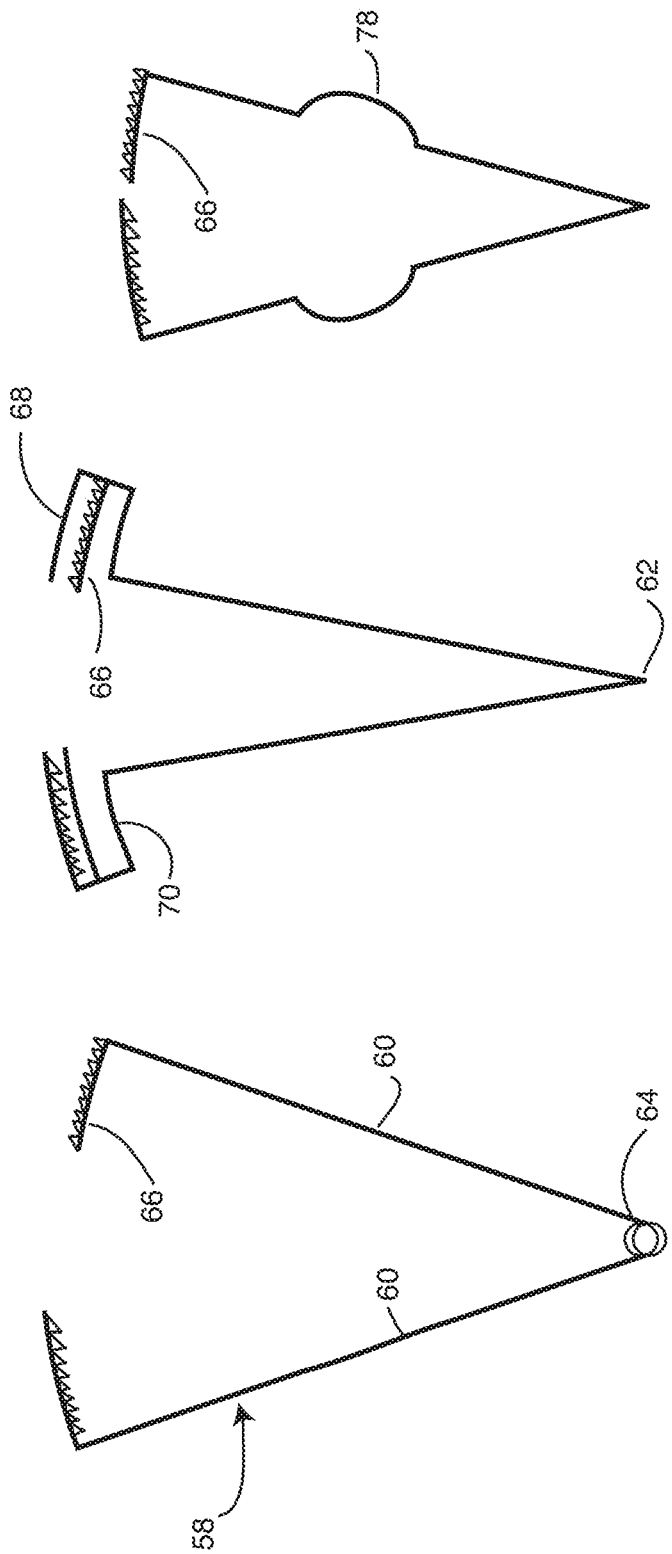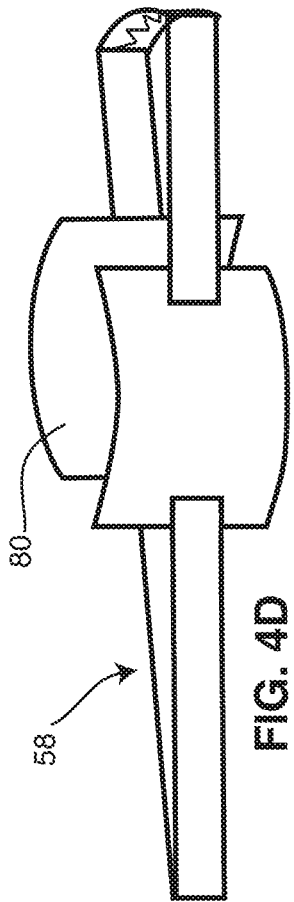

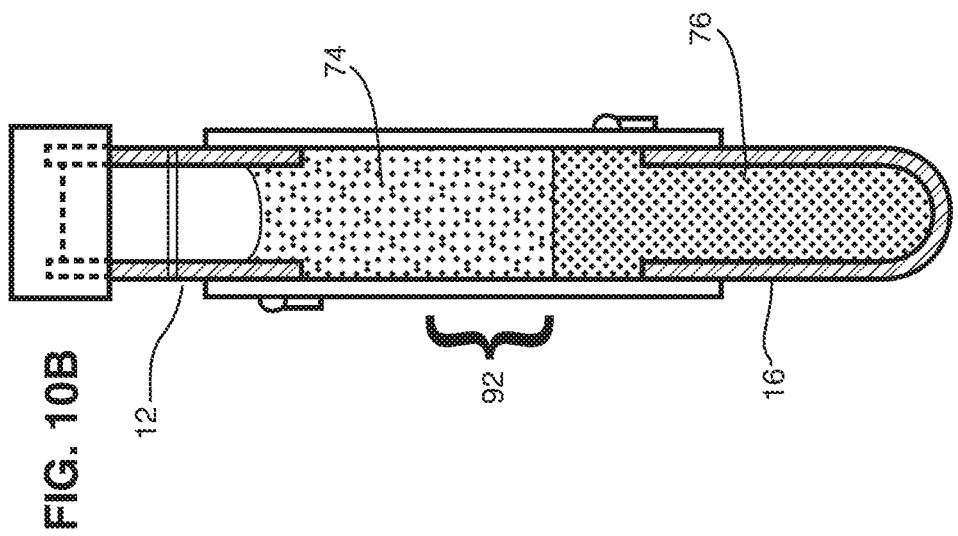
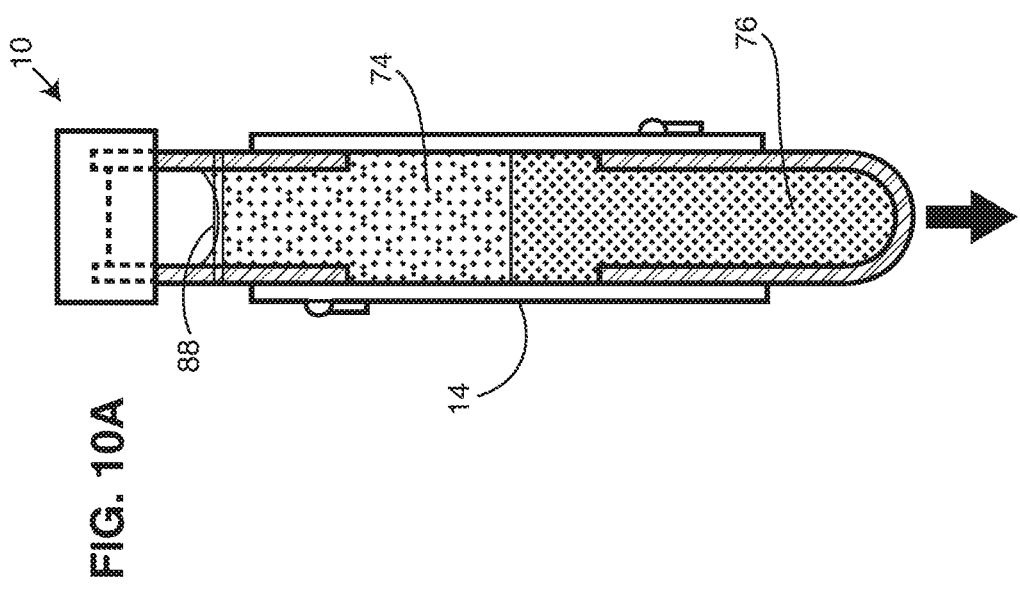

BLOOD COLLECTION TUBE

TECHNICAL FIELD

The present invention relates to a blood collection tube having an elastomeric segment which is constricted to physically separate blood fractions after centrifuging.

DESCRIPTION OF THE RELATED ART

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In modern medicine, the existence of almost every disease, disorder, or condition is ordinarily determined or confirmed by analysis of a sample of blood or other fluids drawn from the patient. Very sophisticated techniques of analysis have been developed and are very effective for this purpose. Typically, in those cases wherein a patient is hospitalized, or presents himself to a well-equipped diagnostic facility, it is common for a blood sample to be taken from the patient at the direction of the physician, and for such sample to be analyzed within a short time after it is taken from the patient.

Ordinarily, a hypodermic syringe is used to pierce the skin and the tip thereof is placed in the vein or artery of the patient, a vacuum is drawn by suitable means to speed filling of the sample container, after a blood sample is taken, the container is subjected to centrifugal force to separate the red cell portion from the plasma portion of the blood. Shortly after this is done, the red blood cell portion or the plasma portion, which are separated from each other by white cells forming the so-called buffy coat, is analyzed according to known techniques. Sometimes, the serum remaining after removal of proteins from the plasma portion is also subjected to analysis. In any case, however, the analysis is ordinarily made within a short time following separation of the blood into these two principal components by centrifugal action. Accordingly, assuming proper test conditions, it is well known that analysis made immediately or very shortly after blood samples are taken is an accurate and very helpful tool for diagnostic or other purposes.

However, blood taken from a patient is, in several important respects, still "alive" in the sense that biological and chemical reactions continue to occur therein even after the blood is removed from the patient. Moreover, it is well known that reactions take place in different, portions of blood samples after separation thereof, that is, a factor, or characteristic of the red cell and WBC portion of a blood sample may react with a component or element of the plasma or serum portion of the blood. Whereas this condition is a normal one during the time the blood is within the body of the patient, and is not harmful per se, it is a condition which adversely affects the accuracy of blood analysis if the analysis is carried out a significant time after removal of the blood from the body of the patient.

Accordingly, in those cases wherein the patient is not presented for blood sampling to a hospital or other facility having an adequate and readily available laboratory, and wherein it is customary for the blood sample to be taken for analysis, to be centrifugally separated into red blood cell and plasma fractions, and then be stored until pick up by a representative of the laboratory wherein the tests are to be taken, the likelihood of an inaccurate analysis is increased. This is especially true in the case of villages, remote areas, and camps, which may have very rudimentary or inaccurate blood analyzers (or no such analyzers) where sending the blood samples to a central testing facility is advantageous.

However, because of the "live" nature of the blood, analysis performed on blood samples collected too long ago may be inaccurate, useless, or misleading, without the red blood cell and plasma fractions being physically separated from one another. Inaccurate results are perhaps dangerous when used as a diagnostic base for administering treatment to the patient whose blood is analyzed. If the blood must be transferred to other containers before analysis, such as by decanting or aspirating the plasma fraction, the chance of contamination is increased, and the procedure becomes more costly and inconvenient to perform.

In view of the forgoing, one objective of the present invention is to provide a blood collection tube having an elastomeric midsection which may be constricted to physically separate the plasma and red blood cell fractions after centrifugation and prior to analysis. This enables blood samples collected from remote areas to be safely preserved during transportation to a central testing facility.

BRIEF SUMMARY OF THE INVENTION

According to a first aspect, the present disclosure relates to a blood collection tube, which has an elastomeric sleeve with a first end connected to a first rigid tube and a second end connected to a second rigid tube. The first rigid tube has a penetrable cap removably attached to an end distal to the elastomeric sleeve, and the second rigid tube has a closed end distal to the elastomeric sleeve. The blood collection tube also has a first ring attached to a first exterior surface of the elastomeric sleeve near the first end and a second ring attached to a second exterior surface of the elastomeric sleeve near the second end, and a pin configured to insert through both first and second rings (when aligned). In addition, the first rigid tube, the elastomeric sleeve, and the second rigid tube are configured to confine an evacuated volume. Rotating the first rigid tube relative to the second rigid tube decreases a longitudinal length of the elastomeric sleeve and constricts an inner diameter of the elastomeric sleeve. The constriction severs fluid communication between the first rigid tube and the second rigid tube.

In one embodiment, the elastomeric sleeve is configured to be in a compressed position so that piercing the penetrable cap allows the elastomeric sleeve to expand, thus providing a material transfer of a fluid into the blood collection tube by suction.

In one embodiment, the first surface and the second surface are located on substantially opposing exterior surfaces.

In one embodiment, the pin comprises a head and a tip, and the tip has a barb or a hook.

In one embodiment, the pin has a plurality of lateral ridges along a longitudinal length, and an interior of the second ring comprises a flexible tab configured to allow movement of the pin in only one direction through the second ring.

In one embodiment, the pin has screw threads configured to engage with an interior of the first ring and/or the second ring.

In one embodiment, the sleeve in an uncompressed state has a substantially cylindrical inner diameter.

In one embodiment, the sleeve in an uncompressed state has a cross-section in a central portion that is substantially perpendicular to a central axis of the sleeve and has an aspect ratio in a range of 1.5:1-15:1.

In one embodiment, the second rigid tube is extendably attached so that a distance between the closed end and the second end may be increased or decreased.

In a further embodiment, the blood collection tube further comprises a clamp. The clamp has two arms extending from a hinge, and each arm terminates with a set of teeth. Each set of teeth is configured to engage with the other set of teeth when an area between the two arms is reduced. The two arms are configured to together pinch the elastomeric sleeve when the elastomeric sleeve is in a constricted position.

In a further embodiment of the clamp, each set of teeth is configured to engage with one another irreversibly in one direction.

In a further embodiment of the claim, each arm of the clamp is linear.

In one embodiment, the first ring, and the second ring are attached near the elastomeric sleeve through a pivotable joint. The pivotable joint is configured to allow the first ring and the second ring to lie flat against an exterior surface of the blood collection tube.

In one embodiment, the first ring and the second ring are attached to a first band and a second band, respectively, and the first band and the second band are each in contact with an exterior circumference of the elastomeric sleeve.

In one embodiment, the first rigid tube and the second rigid tube each have a smaller outer diameter in contact with the first end and the second end of the elastomeric sleeve, respectively.

In one embodiment, the blood collection tube further comprises a color-changing adhesive tape attached to an outside of the first rigid tube, the second rigid tube, and/or the elastomeric sleeve to indicate leaks.

According to a second aspect, the present disclosure relates to a method of using the blood collection tube of the first aspect. This method involves inserting a needle into the penetrable cap, where the needle is in fluid communication with a volume of blood. Then, an aliquot of the blood is transferred into the blood collection tube by suction. Next, the needle is removed from the penetrable cap, and the blood collection tube is centrifuged to produce an erythrocyte enriched layer and a plasma enriched layer from the aliquot of blood. Then, the first rigid tube is rotated relative to the second rigid tube to align the first ring with the second ring. This rotating constricts an inner diameter of the elastomeric sleeve, which limits mixing of the erythrocyte enriched layer and the plasma enriched layer. Next, the pin is inserted through both the first and second rings to secure a position of the first rigid tube relative to the second rigid tube.

In one embodiment, the method further comprises clamping the elastomeric sleeve with a clamp after the rotating.

In one embodiment, the blood collection tube is in a compressed state before the inserting.

In one embodiment, the blood collection tube is twisted or squeezed to increase an internal volume during the transferring.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2A is a cross-section of a blood collection tube in an evacuated state with the elastomeric sleeve curving inwards in a compressed position.

FIG. 2B is the blood collection tube of FIG. 2A following material transfer of a fluid and equalization of interior and exterior pressures.

FIG. 3A shows an embodiment of a pin in the form of a screw.

FIG. 3B shows a straight pin.

FIG. 3C shows a pin having a barb at its tip.

FIG. 3D shows a pin having a plurality of lateral ridges.

FIG. 3E shows a ring having an internal tab configured to form a ratchet mechanism with a type of pin.

FIG. 4A shows one embodiment of a clamp with linear arms and a spring hinge.

FIG. 4B shows another embodiment of a clamp.

FIG. 4C shows another embodiment of a clamp with curved arms.

FIG. 4D shows another embodiment of a clamp having curved opposing faces for grasping and supporting a blood collection tube in a constricted state.

FIG. 10A shows a blood collection tube with a lower volume ratio of plasma to red blood cells.

FIG. 10B shows the blood collection tube of FIG. 10A after extending the second rigid tube to lower the level of the cells.

DETAILED DESCRIPTION OF THE EMBODIMENTS

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like, carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

According to a first aspect, the present disclosure relates to a blood collection tube 10, which has an elastomeric sleeve 14 with a first end connected to a first rigid tube 12 and a second end connected to a second rigid tube 16.

Figure 9C:
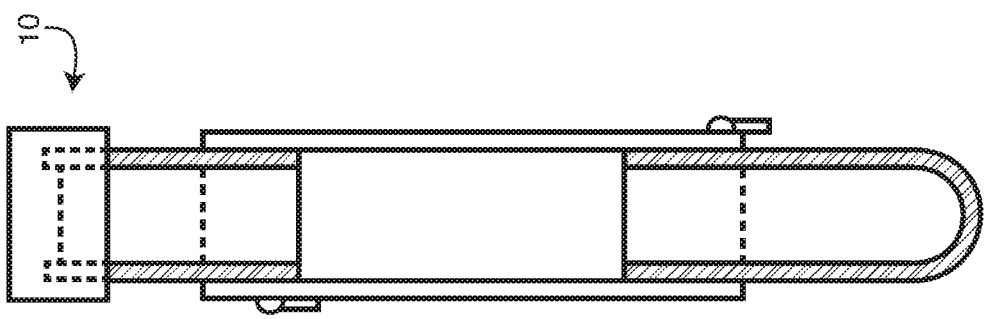
FIG. 9C shows a blood collection tube similar to FIG. 1A but with an extended length.
Figure 9B:
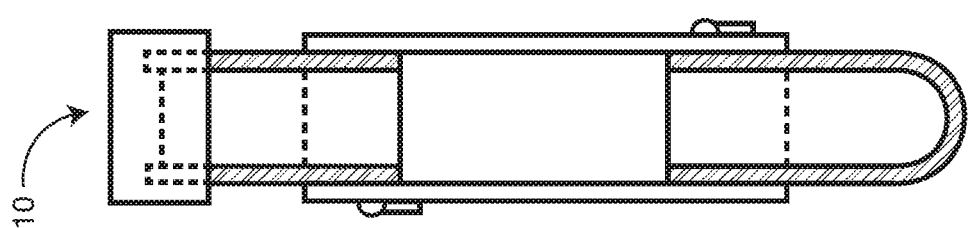
FIG. 9B shows a blood collection tube similar to FIG. 1A.
Figure 9A:
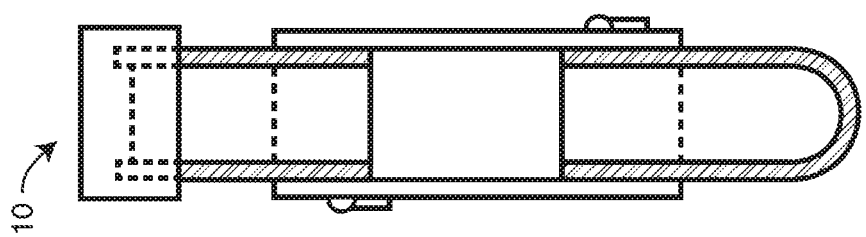
FIG. 9A shows a blood collection tube similar to FIG. 1A but with a shorter length.

The blood collection tube 10 may have a length of 60-120 mm, preferably 70-110 mm, or about 75 mm or about 100 mm. Preferably the overall size and volume of the blood collection tube is similar to conventional tubes used for similar sample collection. The interior volume may be 4-6 mL, or about 5 mL; 6-8 mL, or about 7 mL; 9-11 mL, or about 10 mL. The blood collection tube may be configured to hold a draw volume of 1-2 mL, 1.8-3 mL, 2.5-4.5 mL, 4-6 mL, 5-7 mL, 6-8.5 mL, 8-9.5 mL, or 9-11 mL. FIGS. 9A-9B show blood collection tubes 10 of different lengths and capacities.

Preferably, the blood collection tube is designed to collect a sample of whole blood 18, or anticoagulated blood. However, the tube 10 may collect other biological samples such as a urine, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, or any other physiological fluid or semi-solid. In additional embodiments, the blood collection tube 10 may be used in other applications, such as biological research, forensic science, or food science, in which samples may be centrifuged and decanted at a later time.

In one embodiment, the first and second rigid tubes 12/16 may comprise a variety of different materials including, but not limited to, a ceramic; metals; organic or inorganic materials; and plastic materials, such as polyoxymethylene ("DELRIN®"), polystyrene, acrylonitrile butadiene styrene ("ABS") copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides "aramids"), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, polystyrene, polycarbonate, polypropylene, acrylonitrite butadiene-styrene copolymer, butyl rubber, ethylene propylene diene monomer; and combinations thereof. Preferably the first and second rigid tubes 12/16 comprise polypropylene, polystyrene, or glass, and the first and second rigid tubes 12/16 comprise the same material or materials. However, in an alternative embodiment, the first and second rigid tubes 12/16 comprise different materials.

In one embodiment, the first and/or second rigid tubes 12/16 may have an inside diameter of 6-15 mm, preferably 7-10 mm, more preferably 8.5-8.9 mm, and an outside diameter of 10-17 mm, preferably 12-17 mm, more preferably about 13 mm or about 16 mm. The first and/or second rigid tubes may have a length of 15-45 mm, preferably 20-40 mm, more preferably 22-35 mm. The first and/or second rigid tubes may have a sidewall thickness of 0.1-2 mm, preferably 0.3-1 mm, more preferably 0.4-0.8 mm. In one embodiment, the first and second rigid tubes have similar inside diameters with each other and similar outside diameters with each other. In a related embodiment, the first and second rigid tubes may be formed by severing a single tube that has a single opening and a closed end. The lengths of the first and second rigid tubes 12/16 may be similar or different to each other. The first and/or second rigid tubes 12/16 may have a Shore A hardness (ASTM D2240 00) ranging from approximately 20-80. This range includes all intermediate values and subranges, such as 20, 21, 25, 30, 35, 40, 45, 50, 60, 70, 75, 79, <80 and 80. In one embodiment, the rigid tubes are "rigid" in the sense that they have a tensile modulus, E, of at least 0.2 GPa, preferably at least 0.4 GPa. The tensile modulus is also called "Young's modulus" or "modulus of elasticity." Preferably the first and second rigid tubes 12/16 have cylindrical interior and exterior surfaces, though in alternative embodiments, the tubes may have other curved or angle surfaces, or for instance, may be shaped similarly to a rectangular prism.

In one embodiment, the elastomeric sleeve 14 comprises an elastomer. As defined here, an elastomer is a polymer that displays both viscosity and elasticity, has weak intermolecular forces, and generally has a low Young's modulus and a high failure strain compared with other materials, and may be called more commonly as "rubber." Each of the monomers which link to form the polymer is usually a compound of several elements among carbon, hydrogen, oxygen and silicon. Elastomers are amorphous polymers maintained above their glass transition temperature, so that considerable molecular reconformation without breaking of covalent bonds is feasible. At ambient temperatures, such rubbers are thus relatively soft (E≈3 MPa) and deformable. Elastomeric compounds include natural rubber, polyisoprene (for example, cis-1,4-polyisoprene natural rubber and trans-1,4-polyisoprene gutta-percha), synthetic polyisoprene, polybutadiene, chloroprene rubber (for example, polychloroprene, NEOPRENE, BAYPREN), butyl rubber (copolymer of isobutylene and isoprene), halogenated butyl rubbers, styrene-butadiene rubber, nitrile rubber (copolymer of butadiene and acrylonitrile), hydrogenated nitrile rubbers (for example, THERBAN and ZETPOL), ethylene propylene rubber (a copolymer of ethylene and propylene), ethylene propylene diene rubber (a terpolymer of ethylene, propylene, and a diene-component), epichlorohydrin rubber, polyacrylic rubber, silicone rubber, fluorosilicone rubber, fluoroelastomers (for example, VITON, TECNOFLON, FLUOREL, AFLAS, and DAI-EL), perfluoroelastomers (for example, TECNOFLON PFR, KALREZ, CHEMRAZ, and PERLAST), polyether block amides, chlorosulfonated polyethylene (for example, HYPALON), ethylene-vinyl acetate, thermoplastic elastomers, resilin, elastin, polysulfide rubber, elastolefin, and combinations thereof.

The elastomeric sleeve 14 may have a stiffness value ranging from 100-900 kg/cm$^2$, preferably 300-900 kg/cm$^2$, more preferably 400-600 kg/cm$^2$. The stiffness of the elastomeric sleeve may preferably be measured with the ASTM D1043 method. As used herein, "stiffness" refers to rigidity of an object and the extent to which it resists deformation in response to an applied force. In one embodiment, the elastomeric sleeve 14 may have a tensile modulus, E, of no more than 0.1 GPa, preferably no more than 0.05 GPa. Preferably the elastomeric sleeve 14 is not so flexible as to collapse and sever fluid communication between the first and second rigid tubes 12/16 while centrifuging a sample. The elastomeric sleeve 14 may be considered a soft "tummy" due to its flexibility and location at a central portion of the blood collection tube 10.

As defined here, the blood collection tube 10 or elastomeric sleeve 14 being "constricted" or "in a constricted state" means that the elastomeric sleeve 14 is actively deformed by a user to reduce the interior open diameter or cross-section area of the sleeve, thus limiting the fluid communication from one end of the elastomeric sleeve 14 to the other. Preferably the interior open diameter and/or cross-section area are reduced to zero, meaning that the fluid communication through the sleeve is completely blocked. The elastomeric sleeve 14 may also be partially constricted, meaning that the interior open diameter and/or cross-section are reduced, but not completely reduced to zero.

As defined here, the blood collection tube 10 or elastomeric sleeve 14 being "compressed," means that the sides of the elastomeric sleeve 14 are collapsed or curved inwards due to an exterior, ambient pressure being greater than an internal pressure, for instance, when the blood collection tube is confining an evacuated volume.

In one embodiment, the elastomeric sleeve 14 and first and second rigid tubes 12/16 are transparent and light-transmitting, or translucent. The transparency/translucency of these pieces allow for the volume of sample to be observed and for the separation of phases to be noticed, for instance, after the addition of a coagulation compound, or after centrifuging. In the context, of the present disclosure a material that permits at least 50%, 75%, 80%, 90% or 95% of light of any portion of the light spectrum to pass through may be considered transmissive or transparent. The elastomeric sleeve 14 and first and second rigid tubes 12/16 may preferably be clear to transmit all wavelengths of light. In an alternative embodiment, one or more parts are colored to provide a contrast with the contents for better visual control, or to use color coding to indicate information about the sample collected or about the additive used. One or more parts may be transparent, translucent, opaque, and/or colored as desired. The first rigid tube 12, the second rigid tube 16, and/or the elastomeric sleeve 14 may have volumetric graduations or a measuring line 86.

Figure 1C:
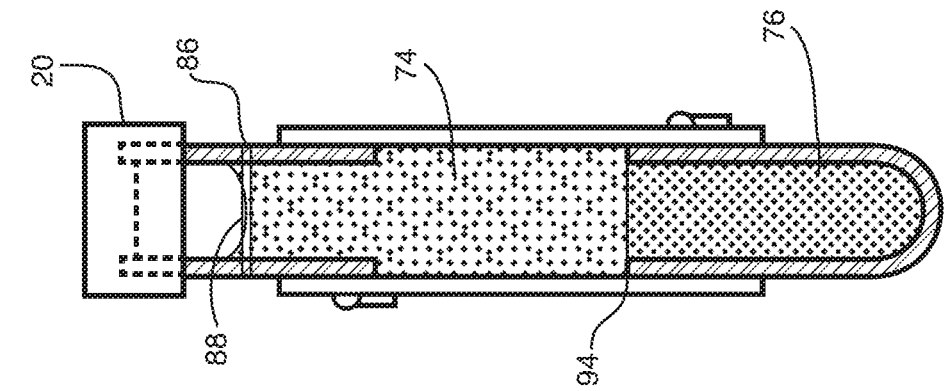
FIG. 1C is the blood collection tube of FIG. 1B following blood collection to a measuring line and centrifugation.
Figure 1B:
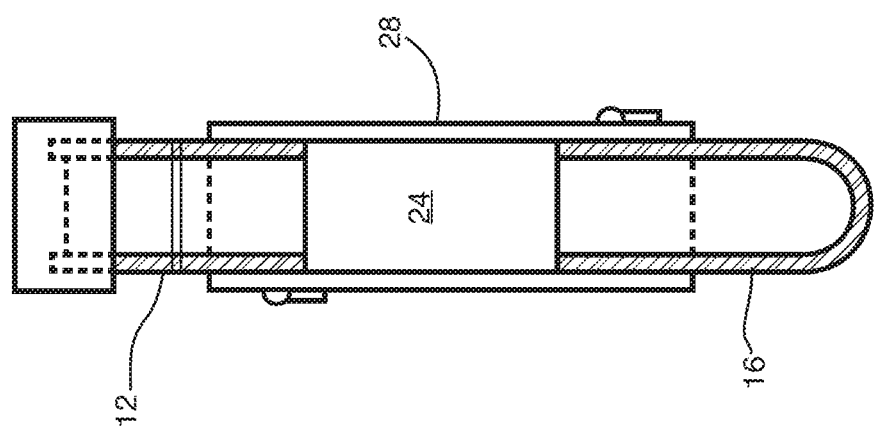
FIG. 1B is a cross-section of the blood collection tube of FIG. 1A.
Figure 1A:
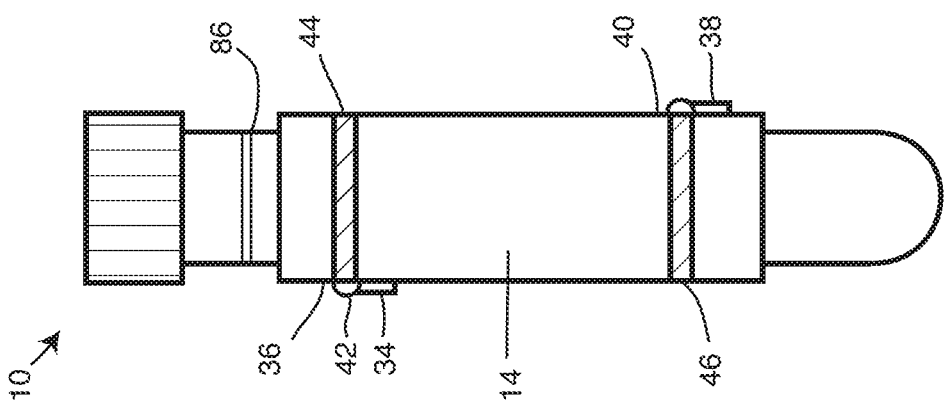
FIG. 1A is a blood collection tube in an unconstricted state without the pin inserted.
Figure 1E:
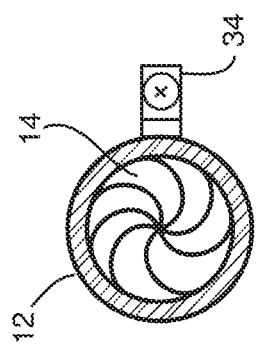
FIG. 1E shows a cross-section of the elastomeric sleeve in a constricted state.
Figure 1D:
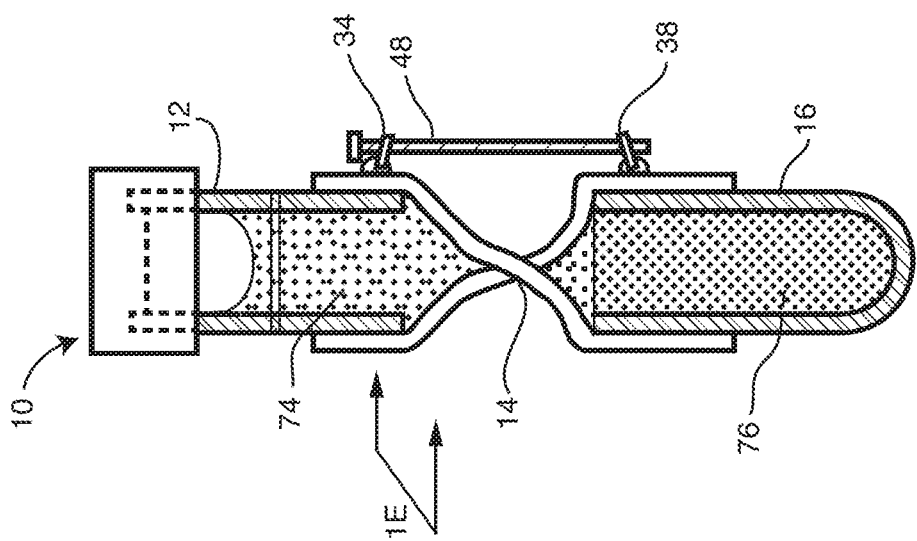
FIG. 1D is the blood collection, tube of FIG. 1B in a constricted state and with the pin inserted.

In one embodiment, the blood collection tube 10 may have a measuring line 86. As shown in FIG. 1C, blood may be filled to this line so following centrifugation, the top of the red blood cell fraction 76 may be approximately at the top 94 of the second rigid tube, assuming a typical blood composition of 45 vol % red blood cells 76 and 55 vol % plasma 74. This measuring line allows a phlebotomist to understand a maximum volume of whole blood that can be collected while maintaining the centrifuged red blood cell fraction 76 below the center of the elastomeric sleeve 14. Here, the elastomeric sleeve 14 is able to be constricted and closed off, as shown in FIG. 1D, while decreasing the tendency of red blood cells to mix with the upper plasma fraction.

The first rigid tube 12 comprises a penetrable cap 20 removably attached to an end distal to the elastomeric sleeve 14, and the second rigid tube has a closed end 22 distal to the elastomeric sleeve 14. In addition, the first rigid tube 12, the elastomeric sleeve 14, and the second rigid tube 16 are configured to confine an evacuated volume 24. The closed end 22 of the second rigid tube may be rounded, such as having a hemispherical shape, or may be flat or pointed. In an alternative embodiment, the second rigid tube 16 may have a removably attached cap similar to the first rigid, tube, rather than a closed end. In another alternative embodiment, the second rigid tube 16 may have a valve or septum.

The penetrable cap 20 is configured for hermetically closing the open end of the first rigid tube 12 to keep the interior blood collection tube under reduced pressure. The penetrable cap 20 may comprise any of the materials as mentioned previously for the rigid tubes 12/16 or elastomeric sleeve 14. In one embodiment, the penetrable cap 20 may removably attached by force fitting into the first rigid tube 12, similar to a rubber stopper. In another embodiment, the penetrable cap 20 may screw onto the first rigid tube by means of screw threads. In a further embodiment, the cap 20 may be attached or sealed to the first rigid tube 12 with an adhesive. The penetrable cap 20 may have a sealing member or septum capable of sealing a puncture opening to maintain liquid-tightness both when a needle 26 or cannula is thrusted into and withdrawn from the penetrable cap. The sealing member or septum may be made of a rubber material such as natural rubber, isoprene rubber, chloroprene rubber and silicone rubber, and a resin such as a thermoplastic elastomer, for instance, styrene-butadiene-styrene (SBS) block copolymer. Other materials described for the elastomeric sleeve 14 may also be used for the sealing member or septum.

In one embodiment, the blood collection tube 10, when capped, confines an evacuated volume 24. The blood collection tube 10 may not enclose a complete vacuum, but may enclose a gas, such as air, nitrogen, or argon, at a lower absolute pressure than the ambient, external pressure. Preferably the blood collection tube 10 encloses an inert gas, such as nitrogen. In one embodiment, the evacuated volume 24 may have an absolute pressure that is 0.01-1 atm, 0.1-0.2 atm, 0.2-0.3 atm, 0.3-0.4 atm, 0.4-0.5 atm, 0.5-0.6 atm, 0.6-0.7 atm, 0.7-0.8 atm, 0.8-0.9 atm, 0.9-1.0 atm, or preferably 0.2-0.8 atm. In one embodiment, the blood collection tube 10 may enclose a volume that is similar or equal to the ambient air pressure. In one embodiment, an evacuated volume 24 within the blood collection tube is able to assist in transferring a fluid (i.e. liquid or gas) from outside to inside the tube, through the penetrable cap 20 if penetrated by a syringe needle 26 or cannula, and if the fluid is at a higher pressure than the evacuated volume. The fluid may be considered to be transferred by suction, or sucked into the tube. In one embodiment, the evacuated volume has an interior pressure chosen so that a liquid, such as blood, is transferred at a draw volume to match a certain volume capacity of the tube. The blood collection tube 10 enclosing an evacuated volume 24 may make its handling similar to a VACUTAINER tube, and may be used with standard blood analyzers.

Figure 5A:
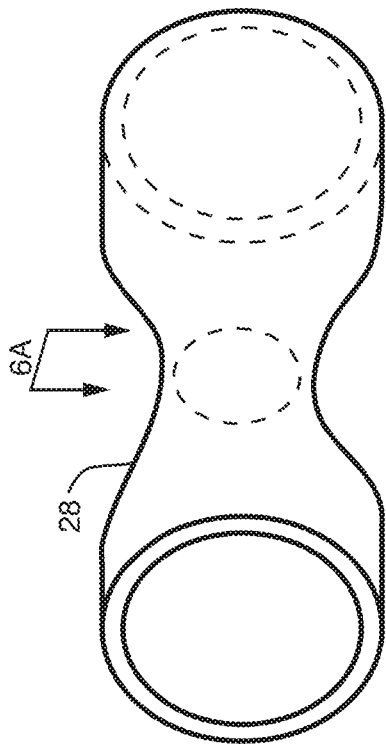
FIG. 5A shows one embodiment of an elastomeric sleeve at equalized interior and exterior pressures.
Figure 5B:
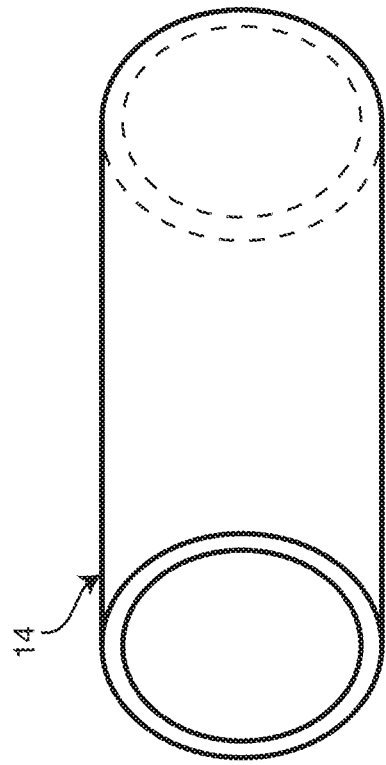
FIG. 5B shows another embodiment of an elastomeric sleeve at equalized interior and exterior pressures, and shaped with a cross-section of smaller area in a central portion.
Figures 6A, 6B, 6C, 6D, 6E, 6F:
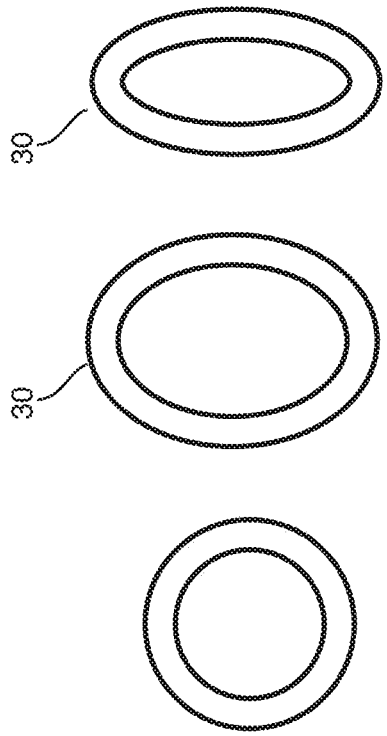
FIG. 6A is the cross-section of FIG. 5B.
FIG. 6B is another example of a smaller cross-section.
FIG. 6C is another example of a smaller cross-section.
FIG. 6D is another example of a smaller cross-section.
FIG. 6E is another example of a smaller cross-section.
FIG. 6F is another example of a smaller cross-section.

In one embodiment, the elastomeric sleeve 14 in an uncompressed state has a substantially cylindrical inner diameter. An example is shown in FIG. 5A, where the elastomeric sleeve 14 is furthermore unconstricted and at equal interior and exterior pressures. Alternatively, the sleeve in an uncompressed and unconstricted state may have a cross-section in a central portion 28 that has a smaller area than either end of the sleeve. The cross-section here is substantially perpendicular to a central axis of the sleeve. Furthermore, as defined here, the central portion 28 of the elastomeric sleeve may be the longitudinal segment just comprising the middle third of the sleeve's length. In other definitions, the central portion 28 may be considered the length of the sleeve that does not overlap with the first or second rigid tubes 12/16, and this length may be larger or smaller than one-third of the tube's length. An embodiment is shown in FIGS. 5B and 6A. Here, the cross-section (FIG. 6A) is circular but has an inner diameter that is 20-80%, preferably 30-70%, more preferably 40-60%, or about 50% of the inner diameter of the elastomeric sleeve ends.

In another embodiment, the elastomeric sleeve 14 in an uncompressed state has a cross-section 30 in a central portion 28 that is substantially perpendicular to a central axis of the sleeve and has an aspect ratio in a range of 1.5:1-15:1, preferably 1.8:1-10:1, more preferably 2.0:1-8:1. In this embodiment, the sleeve in an uncompressed state does not have a substantially-cylindrical inner diameter. Examples of this embodiment are shown by the cross-sections 30 in FIGS. 6B, 6C, 6D, 6E, and 6F. In this embodiment, the elastomeric sleeve 14 may be more easily constricted or sealed, as discussed above for FIG. 5B. However, the cross-sections 30 of this embodiment may enable the elastomeric sleeve to be constricted by the two elongated sides being pinched together, with or without twisting the elastomeric sleeve, and with or without a clamp. These cross-sections may have an elongated shape such as an ellipse (FIGS. 6B and 6C), a pointed elliptical shape having interior corners (such as FIG. 6D, which shape may be similar to two elliptical segments joined together), an oval (FIG. 6F), or some other shape with interior corners that may be amendable to folding its sides together (FIG. 6E). In some cases, the exterior surface of the elastomeric sleeve (or at least a central portion) may resemble a one-sheet hyperboloid.

Figure 7:
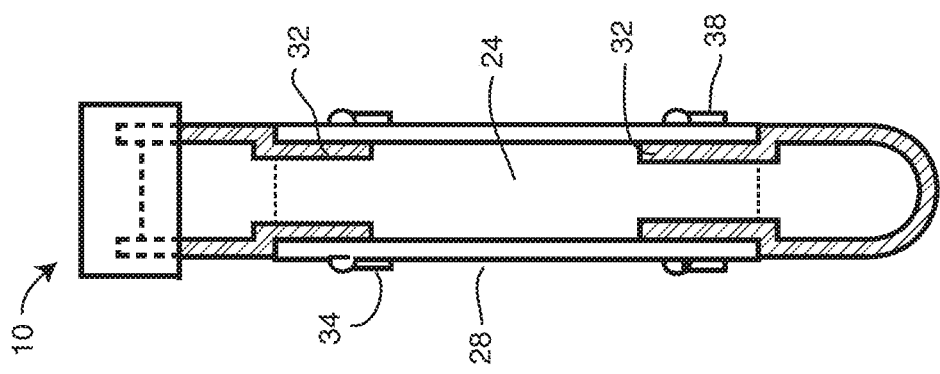
FIG. 7 shows a blood collection tube with the rigid tubes having a segment with a smaller diameter for the contact with the elastomeric sleeve, and having two pairs of rings.

In one embodiment, the ends of the elastomeric sleeve 14 may overlap the rigid tubes by a length of 0.2-4 cm, preferably 0.5-3.5 cm, more preferably 0.7-2.5 cm. In one embodiment, the first rigid tube and the second rigid tube each have a smaller outer diameter 32 in contact with the first end and the second end of the elastomeric sleeve, respectively, as shown in FIG. 7. This feature may provide the advantage of a blood collection tube 10 having a more cylindrical surface profile, similar to a VACUTAINER or other common tubes. For instance, the feature may enable the blood collection tube 10 to fit into a common centrifuge, as the elastomeric sleeve 14 does not add substantially to the outer diameter. The smaller outer diameter 32 may be 50%-98%, preferably 60%-95%, more preferably 75%-90% of the larger outer diameter of the rigid tubes. In this embodiment, the inner diameter of the rigid tubes may not be reduced along the length of the rigid tube, or the inner diameter may be smaller. In an alternative embodiment, only one of the rigid tubes may have a smaller outer diameter in contact with the elastomeric sleeve.

In one embodiment, the first rigid tube and/or the second rigid tube 12/16 is extendably attached to the elastomeric sleeve 14 so that a distance between the closed end and the second end may be increased or decreased. In other words, the first rigid tube may be slidably attached to the first end of the elastomeric sleeve, and/or the second rigid tube may be slidably attached to the second end of the elastomeric sleeve. However, either or both of these attachments to the elastomeric sleeves are intended to have resistance against unintentional slipping of the elastomeric sleeve. In some embodiments, the resistance of this attachment may be modified by bands 44/46 or other structures designed to provide tension. In other embodiments, the elastomeric sleeve and either rigid tube may connect with a tongue and groove joint, in order to provide resistance against twisting motion, but also to allow some amount of extendibility. Similarly, in some embodiments, either rigid tube or elastomeric sleeve may have concentric ridges or grooves on the inner surfaces. These concentric ridges or grooves may help provide resistance and/or may provide a tactile sensation when extending. In one embodiment, the extendable movement may be used to adjust the height or volume of the blood collection tube. This in turn may adjust the position of the blood collection tube contents in relation to either rigid tube 12/16, the cap 20, and/or the elastomeric sleeve 14. Preferably this adjustment is done after collecting a sample, preferably after both collecting and centrifuging, but before twisting or closing off the elastomeric sleeve 14.

In a preferred embodiment, the second rigid tube 16 is extendably attached to the elastomeric sleeve 14 so that a distance between the closed end 22 of the second rigid tube and the second end of the elastomeric sleeve 14 may be increased or decreased. In other words, the blood collection tube 10 may be made longer or shorter without twisting or otherwise changing the cross-section of the elastomeric sleeve. An example is shown in FIGS. 10A and 10B. FIG. 10A shows a blood collection tube 10 holding a blood sample after centrifuging. Noticeably, this sample has a higher volume ratio of red blood cells 76 to plasma 74 than is typical of a whole blood sample from a healthy individual, and this high volume ratio may result from conditions such as polycythemia or leukemia. As FIG. 10A indicates, the boundary between the red blood cells 76 and the plasma 74 is near the center of the elastomeric sleeve, where twisting, the blood collection tube to seal off the phases may unwantedly mix red blood cells with the plasma fraction. FIG. 10B shows the tube of FIG. 10A after the second rigid tube 16 is extended downward in the direction of the arrow. This manual adjustment allows the middle area 92 of the elastomeric sleeve to now predominantly contact the plasma 74 fraction, so that the blood collection tube may be twisted and closed without inadvertently transferring red blood cells into the plasma.

The blood collection tube 10 also has a first ring 34 attached to a first exterior surface 36 of the elastomeric sleeve near the first end and a second ring 38 attached to a second exterior surface 40 of the elastomeric sleeve near the second end. Each ring 34/38 may be attached 2-30 mm, preferably 4-20 mm, more preferably 5-18 mm from the nearest end of the elastomeric sleeve 14. In one embodiment, the rings 34/38 may be shaped like a torus, a nut, or may be elongated in the form of a sleeve. The rings 34/38 may have an inner diameter of 0.5-5 mm, preferably 1.0-3 mm, an outer diameter of 4-15 mm, preferably 5-10 mm, and a thickness of 0.5-4 mm, preferably 1-3 mm. In some embodiments, the ring may be rectangular with a rectangular opening.

In one embodiment, the first surface 36 and the second surface 40 are located on substantially opposing exterior surfaces. In a further embodiment, the first and second surface 36/40 are parts of cylindrical surfaces. Here, the first and second surfaces 36/40 being on substantially opposing exterior surfaces means that the rings 34/38 form a dihedral angle with the central axis of the rigid tubes that is 150°-180°, preferably 160°-180°, more preferably 170°-180°, or about 180°. The dihedral angle, in other words, is the angle between two planes: the plane by the first surface 36 and the central axis, and the plane formed by the second surface 40 and the central axis. In this embodiment, the rigid tubes 12/16 may be rotated about 180° or about 540° to constrict the elastomeric sleeve 14 and align the two rings 34/38. The rings may be adhered to, or form part of, the elastomeric sleeve. Alternatively, the rings may be attached to either one or both rigid tubes. In one embodiment, the first ring 34 and the second ring 38 are attached near the elastomeric sleeve 14 through a pivotable joint 42. The pivotable joint 42 is configured to allow the first ring 34 and the second ring 38 to lie flat against an exterior surface of the blood collection tube. The rings lying flat reduces the surface profile of the blood collection tube 10 and allows the tube 10 to more easily fit within a centrifuge, rack, or some other tube holder. In a further embodiment, a part of the elastomeric sleeve 14 or either rigid tube 12/16 may have a depressed surface for a ring to lie inside, further reducing the surface profile. Preferably the rings 34/38 are able to be pivoted to a perpendicular angle with the sleeve 14, and may have a freedom of movement of at least 50°, preferably at least 70°, more preferably at least 80° from the perpendicular angle in either direction along the length of the blood collection tube. In one embodiment, the pivotable join 42 may comprise two parts joined as a hinge, though in another embodiment, the hinge may only be one part, as a living hinge.

Figure 1H:
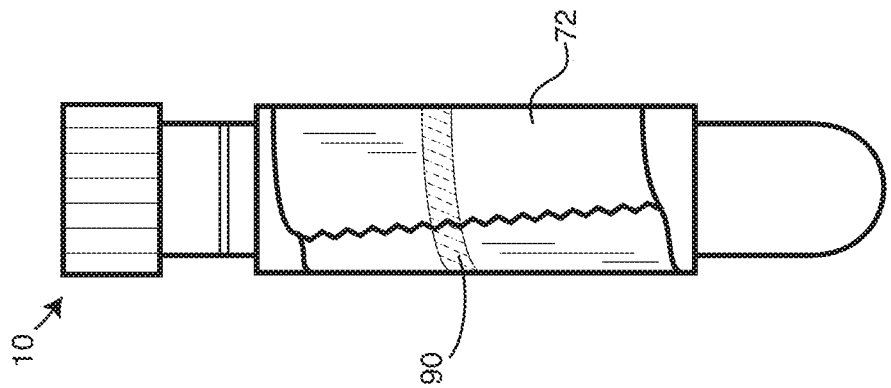
FIG. 1H is the blood collection tube of FIG. 1G after wrapping.
Figure 1G:
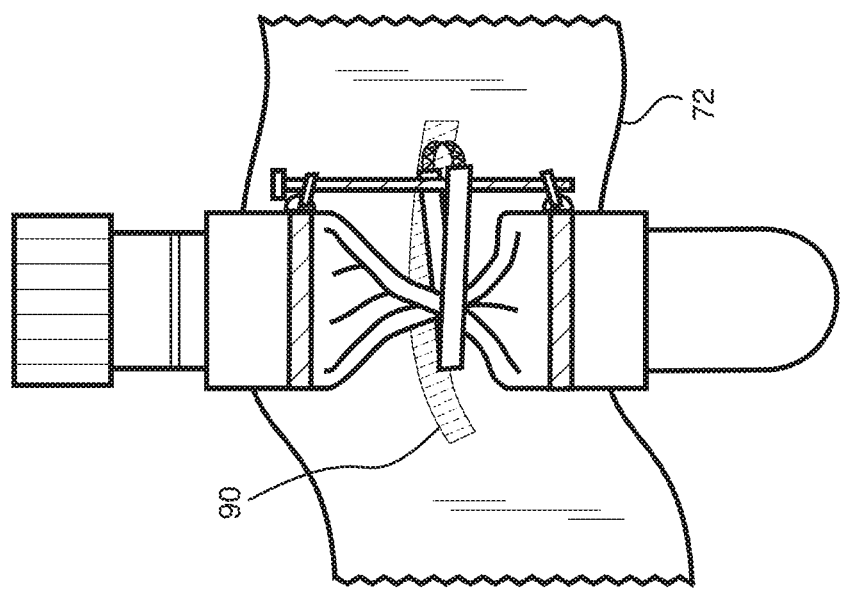
FIG. 1G is the blood collection tube of FIG. 1F being wrapped by the adhesive tape and pH paper.
Figure 1F:
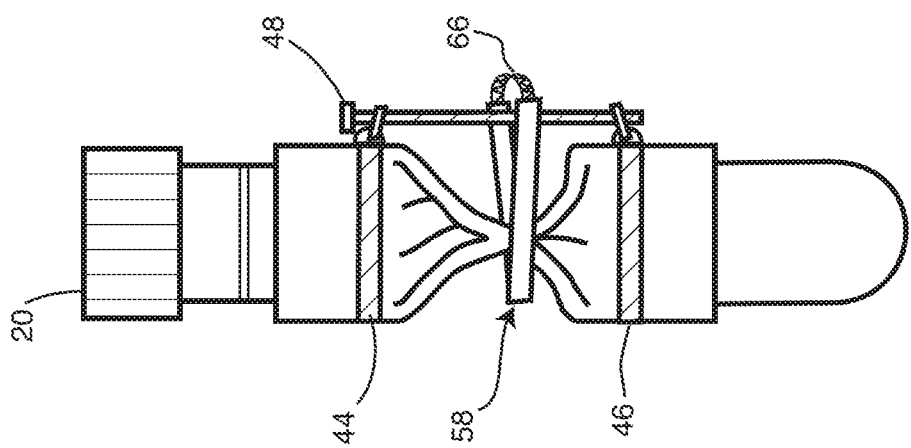
FIG. 1F is the blood collection tube in a constricted state with the pin and a clamp.

In one embodiment, the first ring 34 and the second ring 38 are attached to a first band 44 and a second band 46, respectively, and the first band and the second band are each in contact with an exterior circumference of the elastomeric sleeve. An example of this is shown in FIGS. 1A and 1F. Here, the bands 44/46 may each be attached around a circumference that is 2-30 mm, preferably 4-20 mm, more preferably 5-18 mm from the nearest end of the elastomeric sleeve. Preferably the bands are 44/46 attached around a circumference of the sleeve 14 that also overlaps a rigid tube. In a further embodiment, the bands 44/46 may be tightened not only to secure to the elastomeric sleeve 14, but to secure the elastomeric sleeve to the rigid tubes 12/16. Each band may have a width of 1-10 mm, preferably 2-8 mm, more preferably 3-7 mm. The bands 44/46 may be made of a metal, such as stainless steel, or may be made of a material described previously for the elastomeric sleeve and the rigid tube. In another embodiment, the bands 44/46 may instead be metal wires or a zip tie. In some embodiments, the interior surface of the bands in contact with the elastomeric sleeve may be textured to have a better grip.

The blood collection tube 10 also comprises a pin 48 configured to insert through both first and second rings 34/38, preferably when the rings are aligned and the elastomeric sleeve is constricted, in order to hold the blood collection tube in a constricted state. The pin 48 may be made of a metal, or any of the materials previously mentioned for the rigid tube. The pin 48 may have a length of 0.5-9 cm, preferably 1-6 cm, more preferably 2-5 cm, and a cross-section area that is at least 50%, preferably at least 80% of the area if the first ring opening and the second ring opening. The pin 48 may have a head similar to a nail or screw head, or a tab for easier handling and to keep the pin from completely passing through the rings.

In one embodiment, the pin 48 comprises a head and a tip, and the tip has a barb 50 or a hook. An example of a pin 48 with a barb 50 at its tip is shown in FIG. 3C. In another embodiment, the tip may have a plurality of barbs. Preferably the barb or plurality of barbs prevents the pin 48 from being removed from the second ring or both rings.

In one embodiment, the pin 48 has a plurality of lateral ridges 52 along a longitudinal length. The lateral ridges 52 may be spaced by a distance of 0.1-5 mm, preferably 0.3-2 mm and may also be considered gear teeth. An example of such pin 48 with lateral ridges 52 is shown in FIG. 3D. With this embodiment, an interior of the second ring also comprises a flexible tab 54 configured to allow movement of the pin 48 in only one direction through the second ring 38 by forming a ratchet mechanism. An example of such ring is shown in FIG. 3E. This type of pin and ring engagement may be substantially similar to a zip tie, cable tie, wire tie, hose tie, steggel tie, or zap strap. In some embodiments, the first ring may also have a similar flexible tab to form a ratchet mechanism with the pin. The pin's movement in one direction, whether the pin 48 has a barb, forms part of a ratchet mechanism, or has some other structure, is intended to retain the blood collection tube 10 in a constricted state permanently. In one embodiment, a blood collection tube 10 may have more than one pair of rings, for instance two or three pairs. FIG. 7 shows a blood collection tube 10 with two pairs of rings. Fastening a constricted blood collection tube with more than one pin into more than one pair of rings may provide additional stability. However, in another embodiment, a blood collection tube 10 may have only one pair of rings.

In one embodiment, the pin 48 has screw threads 56 configured to engage with an interior of the first ring 34 and/or the second ring 38. An example is shown in FIG. 3A. In this instance, the pin 48 may be considered to be a screw and inserted as such. In a related embodiment, where the pin has straight, untextured sides, the pin 48 may be thought of as a nail.

Figure 8B:
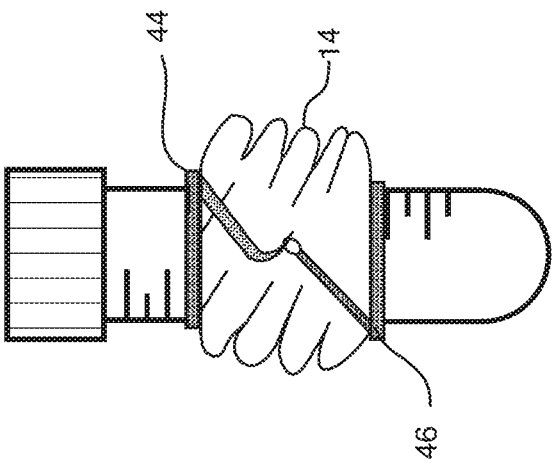
FIG. 8B shows the blood collection tube of FIG. 8A in a constricted and latched state.
Figure 8A:
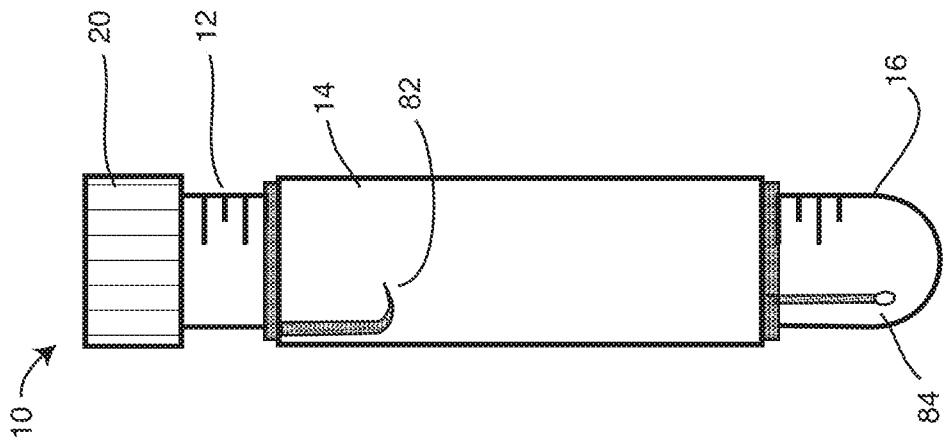
FIG. 8A shows a blood collection tube with a different latching mechanism.

In another embodiment, rather than inserting a pin, a wire tie or a string may be threaded through the first and second rings 34/38 and then tied. In alternative embodiments, other fastening mechanisms may be adapted to the blood collection tube 10. One example is shown in FIGS. 8A and 8B, which show a blood collection tube 10 having a hook 82 and an eye 84. In this alternative embodiment, the hook and eye are each attached to a band, where the band is in direct contact with a circumference of each rigid tube. Other fastening mechanisms may involve inserting the blood collection tube 10 into a tubular rigid frame or brace with a helical groove on its side. A short pin protruding from a rigid tube 12/16 is guided through the groove to twist and constrict the elastomeric sleeve, and then hold the blood collection tube in a constricted position.

In one embodiment, the elastomeric sleeve 14 is configured to be in a compressed position so that piercing the penetrable cap 20 allows the elastomeric sleeve 14 to expand, thus providing a material transfer of a fluid into the blood collection tube 10 by suction. In this embodiment, the elastomeric sleeve 14 is curved inwards with an increased tension, due to forces from the ambient air pressure with respect to the evacuated volume 24. The sleeve 14 being curved inwards may be considered a compressed position, and when a needle or cannula pierces through the penetrable cap, the elastomeric sleeve 14 expands towards a more cylindrical shape due to a release of surface tension and equalization of interior and exterior pressures. In a related embodiment, the elastomeric sleeve may be compressed or shortened vertically, and then expand to its full length following material transfer. Similarly, in some embodiments, a part of the penetrable cap may be curved inwards and then expand upon piercing for the same reasons.

In another embodiment, the elastomeric sleeve 14 may be formed with a central cross-section 30 of reduced area and elongated shape, as described previously and shown in FIGS. 6B-6F. In this embodiment, the elastomeric sleeve 14 may be pinched at the widest part on the cross-section, which increases the area of the cross-section and thus increases the interior volume. This increase in interior volume may then cause material transfer by suction. In some embodiments, an elastomeric sleeve 14 may be formed with a decreased cross-section area and then further compressed or flattened due to the decreased pressure of the interior volume. In these embodiments, some amount of material transfer may occur on its own by suction, and then an additional material transfer may be possible by pinching the cross-section along its longest width to form a larger area, and thus larger volume.

In one embodiment, rotating the first rigid tube 12 relative to the second rigid tube 16 decreases a longitudinal length of the elastomeric sleeve 14 and constricts an inner diameter of the elastomeric sleeve. The constriction severs fluid communication between the first rigid tube 12 and the second rigid tube 16 by twisting the elastomeric sleeve shut, such as that shown in FIG. 1E, where the elastomeric sleeve 14 constricts completely closed. Here, "severs fluid communication" between first rigid tube 12 and the second rigid tube 16 means that the interior of the first rigid tube is sealed from the interior of the second rigid tube, and vice versa. In one embodiment, the first rigid tube 12 may be rotated 170°-190°, or about 180° relative to the second rigid tube 16, and rotated in either direction (i.e. right-handed or left-handed turn). Preferably the rotation is to align the rings 34/38 or some other fastening mechanism to keep the blood collection tube in a constricted state. In other embodiments, the first rigid 12 tube may be rotated by 70°-170°, 80°-130°, 190°-550°, 260°-545°, or 350°-460°, relative to the second rigid tube 16, in either direction. In one embodiment, the first rigid tube 12 may be configured to be rotated in one direction only. In other embodiments, the elastomeric sleeve 14 may not be constricted completely closed, but may have a smallest inner diameter of 1-50% or 2-25% of its initial smallest inner diameter. Here, a clamp 58 or some other device may be used to further reduce the cross-section area and completely close the elastomeric sleeve. Additionally, the rotating decreases the length of the blood collection tube by shortening the length of the elastomeric sleeve 14. The elastomeric sleeve in a constricted or partially constricted state may have a length that is 20-90%, preferably 30-80% of the initial length of the unconstricted elastomeric sleeve.

In an alternative embodiment, the blood collection tube 10, either constricted, partially constricted, or unconstricted by twisting, may be bent at the elastomeric sleeve 14 to bring the rigid tubes closer to one another. This folding or bending at the elastomeric sleeve 14 may also serve a similar purpose of severing fluid communication between the interiors of the rigid tubes, and a fastening mechanism may be used to hold the rigid tubes in this position relative to each other.

In a further embodiment, the blood collection tube 10 further comprises a clamp 58. In some embodiments, a blood collection tube with a clamp may be considered a blood collection tube assembly. The clamp 58 may be, but is not limited to, a collet clamp, an O-ring, a pipe clamp, a hose clamp, a spring clamp, a pair of tongs, a screw clamp, a strap clamp, locking forceps, pincers, or a tie. The arms of the clamp may function as first or second class levers. In alternative embodiments, a clamp 58 may be applied to the blood collection tube 10 to constrict the elastomeric sleeve 14 without the tubes being rotated relative to each other and without inserting a pin 48. In one embodiment, the clamp may support the first rigid tube 12 from bending over. In a related embodiment, the clamp may support one or more pins inserted into the rings.

In one embodiment, the clamp 58 has two arms 60 extending from a hinge 62. The arms 60 may have a length of 2-7 cm, preferably 3-6 cm, more preferably 3.5-5 cm, and the arms 60 may be straight and linear, curved, or may have a combination of angled or curved portions. FIG. 4C shows curved arms 78. The two arms 60 are configured to together pinch the elastomeric sleeve 14 when the elastomeric sleeve 14 is in a constricted position. In one embodiment, the arms 60 may be similar to a rigid wire, though in some embodiments, the arms may have flat surfaces, or even cylindrical surfaces 80 as in FIG. 4D, to better grip the elastomeric sleeve 14. The flat or cylindrical surfaces may have a height of 0.5-5 cm, preferably 1-4 cm. The hinge 62 may be formed with or without a spring 64.

In one embodiment of the clamp 58, each arm 60 terminates with a set of teeth 66. Each set of teeth is configured to engage with the other set of teeth when an area between the two arms 60 is reduced (i.e., when the clamp is being closed). Each set of teeth 66 may have a length of 0.5-3 cm, preferably 0.8-2 cm. Each tooth may have a width of 0.3-5 mm, preferably 0.5-4 mm, and a height of 0.1-4 mm, preferably 0.4-3 mm. Each set of teeth may further have a guard 68 to protect the teeth and/or guide the alignment of one set of teeth with the other. The guard 68 may have a length of at least 50%, preferably at least 75%, more preferably at least 90% the length of the set of teeth, and the guard 68 may be spaced by a distance of 1-10 mm, preferably 2-5 mm from the set of teeth. Such guard 68 is shown in FIG. 4B. Additionally, the set of teeth 66 may be offset from the arms 60 of the clamp, also shown in FIG. 4B. The set of teeth may be offset with linear segments 70 having lengths of 0.2-2 cm, preferably 0.4-1 cm. In a preferred embodiment, the clamp 58 comprises a metal, though the clamp may also comprise any other material as mentioned for the rigid tubes.

In a further embodiment of the clamp 58, each set of teeth is 66 configured to engage with one another irreversibly in one direction (for instance, when they slide past each other), and this may be considered a ratchet mechanism. Similar to what was discussed previously for the pin 48 having a barb or forming a zip tie, the irreversible closing of the clamp is intended to hold the blood collection tube 10 permanently in a constricted state. In another embodiment, each set of teeth 66 may engage and slide past each other in only one direction, but may also be released and opened, similar to a locking surgical clamp.

In one embodiment, the interior surface of the elastomeric sleeve may comprise an adhesive. In this embodiment, constricting the elastomeric sleeve causes the interior surfaces to directly contact each other, which leads to the interior surfaces adhering to one another. Preferably, an adhesive bond is formed of a strength sufficient to hold the elastomeric sleeve in a constricted state without the pin and without the clamp, though in some embodiments, the pin and/or the clamp may also be used. In one embodiment, an adhesive may be impregnated into cells within the elastomeric sleeve in order to reduce its contact with the blood sample. Here, constricting the elastomeric sleeve disrupts and breaks the cells, releasing the adhesive.

In one embodiment, the blood collection tube 10 further comprises a color-changing adhesive tape 72 attached to an outside of the first rigid tube, the second rigid tube, and/or the elastomeric sleeve to indicate leaks. The color-changing adhesive tape 72 may have a width of 3-25 mm, preferably 5-15 mm, and a length of 10-70 mm, preferably 15-50 mm, and either a portion or all of the adhesive tape may have color-changing ability. Where the adhesive tape is not completely color changing, the non-color changing part may be colorless, clear, translucent, or opaque. In one embodiment, a label or some other sticker may be used as the adhesive tape, and may comprise printed or written information about the sample or patient. In one embodiment, the adhesive tape 72 may have a width similar to the length of the elastomeric sleeve in a constricted state. The adhesive tape 72 may have a length that allows it to be wrapped around the blood collection tube a total of 1 revolution, 1-3 revolutions, preferably 1.1-2.0 revolutions, more preferably 1.2-1.8 revolutions. FIGS. 1G and 1H show a blood collection tube 10 having the adhesive tape attached to the elastomeric sleeve 14. The adhesive tape 72 may comprise a pH indicator or a moisture sensitive dye to indicate contact with a liquid or moisture by changing colors. In one embodiment, the adhesive tape 72 only changes color based on moisture or liquid contacting an interior surface. The adhesive tape 72 may also secure together parts of the blood collection tube 10. The adhesive tape 72 may comprise a cellulose derivative, such as cellulose acetate, or may be any plastic or elastomeric material as mentioned previously for the rigid tubes 12/16 or elastomeric sleeve 14. In another embodiment, an exterior surface of the blood collection tube may have a pH indicator or a moisture sensitive dye for similar purposes.

In a preferred embodiment, as shown in FIGS. 1G and 1H, the color-changing adhesive tape 72 comprises pH paper 90 at the sticky side. Besides the pH paper, the adhesive tape is otherwise transparent or colorless. The adhesive tape is wrapped around the tube and is about the length of the constricted elastomeric sleeve, or 30-110%, or 40-90%, or 50-80% the length of the constricted elastomeric sleeve. The adhesive tape may be positioned so that the pH paper 90 is located near the clamp 58 and the narrowest constriction of the elastomeric sleeve as shown in FIG. 1G, however, in other embodiments, the pH paper may be placed at other positions on the elastomeric sleeve, or more than one pH paper may be present. In one embodiment, the pH paper is yellow, but turns to a green color when in contact with blood, due to the blood's alkalinity (pH in a range of 7.3-7.4). Thus, when the adhesive tape 72 and pH paper 90 are secured around the elastomeric sleeve 14 as in FIG. 1H, any leaks of plasma or red blood cells from the elastomeric sleeve are contained between the elastomeric sleeve and the adhesive tape. In this space, leaked plasma and/or red blood cells are in fluid communication with the pH paper 90 surface, and create a yellow to green color change which is propagated through the thickness of the pH paper. This color change is then visible from the opposite side, or outer surface, of the adhesive tape 72. In an alternative embodiment, an adhesive tape may serve the purpose of holding the elastomeric sleeve in a constricted state. In further embodiments, this holding by the adhesive tape may be when a clamp 58 or other fastening structures are not used with the blood collection tube.

In one embodiment, the interior of the blood collection tube 10 may be coated with a surface treatment agent or other compounds. In the case of blood collection tubes for use in coagulating blood or counting red or white blood cells, it is preferable to treat the inner surface to be hydrophilic so as to prevent blood cells from adhering to the inner surface. This treatment may be carried out by coating the inner surface with hydrophilic materials such as water-soluble silicone resin, spray-coated silica, polyvinyl alcohol, or polyvinyl pyrrolidone (PVP). An anticoagulant agent such as sodium heparin, lithium heparin, and/or $K_2$EDTA may be applied to the inner surface or may be contained in bottom of the blood collection tube. Alternatively, a blood-coagulation promoter may be used instead. In other embodiments, the blood collection tube may hold a buffered sodium citrate solution, a glycolytic inhibitor, sodium fluoride, potassium oxalate, $K_3$EDTA, theophylline, adenosine, dipyridamole, potassium sorbite, or a plasma separation gel.

In one embodiment, the blood collection tube 10 may further comprise a delineation fluid. A delineation fluid may be used to provide further separation between the target material and any non-target material above and/or below the target material. For example, to further separate a buffy coat (i.e. white blood cells and platelets) from plasma 74, or to separate a buffy coat from red blood cells 76. The delineation fluid may have a density greater than or less than the target material. For example, when it is desirous to further separate a buffy coat and red blood cells, the delineation fluid may have a density greater than the buffy coat but less than the red blood cells. The delineation fluid may be miscible or immiscible with a suspension fluid and inert with respect to suspension materials. The density of the delineation fluid may be static (e.g. remaining constant) or dynamic (e.g. changing based on outside or environmental conditions, including pressure or temperature). The delineation fluid may also provide an area in which to constrict the elastomeric sleeve, as there is greater delineation and separation between the buffy coat and the red blood cells. Examples of suitable delineation fluids include, but are not limited to, solution of colloidal silica particles coated with polyvinylpyrrolidone (e.g. Percoll), polysaccharide solution (e.g. Ficoll), iodixanol, cesium chloride, sucrose, sugar-based solutions, polymer-based solutions, surfactants, an organic solvent, a liquid wax, an oil, a gas, and combinations thereof; olive oil, mineral oil, silicone oil, chill-out liquid wax, paraffin wax, microcrystalline waxes, soy and palm waxes, candle waxes, thermoset waxes, hot melt adhesives, atactic polypropylene and polyolefin compounds, petroleum waxes, dental waxes, animal waxes, vegetable waxes, mineral waxes, petroleum waxes, and synthetic waxes, such as ethylenic polymers, chlorinated naphthalenes or hydrocarbon-type waxes; immersion oil, mineral oil, paraffin oil, silicon oil, fluorosilicone, perfluorodecalin, perfluoroperhydrophenanthrene, perfluorooctylbromide, and combinations thereof; organic solvents such as 1,4-dioxane, acetonitrile, ethyl acetate, tert-butanol, cyclohexanone, methylene chloride, tert-amyl alcohol, tert-butyl methyl ether, butyl acetate, hexanol, nitrobenzene, toluene, octanol, octane, propylene carbonate, tetramethylene sulfones, and ionic liquids; perfluoroketones, such as perfluorocyclopentanone and perfluorocyclohexanone, fluorinated ketones, hydrofluoroethers, hydrofluorocarbons, perfluorocarbons, perfluoropolyethers, silicon and silicon-based liquids, such as phenylmethyl siloxane. A delineation fluid may also be considered a plasma separator.

In one embodiment, the blood collection tube 10 may comprise a blood coagulation promoter, which may include silica sands, crystal silica, diatomite, fine glass particles, kaolin, bentonite, hectorite, protamine sulfate, thrombin, or a similar compound, having particle diameters of 0.4 to 20 µm, or less than 5 µm, or an average particle diameter of about 1.1 µm.

According to a second aspect, the present disclosure relates to a method of using the blood collection tube 10 of the first aspect. This method involves inserting a needle 26 into the penetrable cap 20, where the needle 26 is in fluid communication with a volume of blood. In one embodiment, the needle is within a tube holder and in fluid communication with a patient's blood vessel. In another embodiment, the needle is in fluid communication with a syringe holding a sample of blood taken from a patient. In one embodiment, the blood collection tube 10 is in a compressed state before inserting the needle 26 into the penetrable cap 20.

Then, an aliquot of the blood is transferred into the blood collection tube 10 by suction. Here, the needle 26 may be kept within the penetrable cap 20 until the interior and exterior pressures equalize and the blood flow rate slows. Alternatively, the needle 26 may be removed prior to that time, or when a certain volume is obtained. In one embodiment, the blood collection tube 10 is twisted, squeezed, or pulled to increase an internal volume during the transferring, which creates a suction force. For instance, the sides of the elastomeric sleeve 14 may be pinched to increase a cross-section area which increases the internal volume. In alternative embodiments, blood may be transferred to a blood collection tube that does not have suction, or an external source of pressure or suction may be applied. In one embodiment, the tube may be filled with blood up to a measuring line 86.

Next, the needle 26 is removed from the penetrable cap 20, which preferably seals to protect the sample against loss or contamination. The blood collection tube 10 is then centrifuged to produce an erythrocyte enriched layer 76 and a plasma enriched layer 74 from the aliquot of blood. In one embodiment, a blood sample may be clotted or reacted with a compound before centrifuging. The centrifuging may be in a horizontal head (swinging bucket) type centrifuge or in a fixed angle type centrifuge. The blood collection tube may be centrifuged at a relative centrifugal force (RCF) of 150-3,000×g, preferably 1,000-2,500×g, more preferably 1,200-1,300×g for a time period of 5-30 min, preferably 8-20 min, or about 10 min. In other embodiments, the blood collection tube 10 may be centrifuged with any time and speed known to a person having ordinary skill in the art of phlebotomy.

The "erythrocyte enriched layer" may be considered a red blood cell fraction 76, and, after centrifuging, is located below the plasma fraction 74. A blood sample immediately after centrifugation may comprise about 45 vol % red blood cell fraction 76 in the bottom of the tube and about 55 vol % plasma fraction 74 in the top of the tube. In certain health conditions or sample collections, the volume percentages may deviate from 45 vol % and 55 vol %. Between the plasma and red blood cell fractions there may exist a "buffy coat" layer of white blood cells and platelets and may make up 0-1 vol % of the total volume of the blood sample. In some cases, the red blood cell fraction 76 may not be 100% red blood cells and the plasma fraction 74 may not be 100% plasma. Either fraction may mix with small amounts, for instance 1 vol % relative to a total volume of the sample, of the other fraction, or with white cells, platelets, or other biological material. In one embodiment, the handling of the blood collection tube 10 up to and including the centrifugation step may be substantially similar to the handling of other blood collection tubes, such as BD VACUTAINER tubes. In one embodiment, the blood collection tube 10 may completely replace VACUTAINER tubes and other similar red-top and gel tubes commonly used for blood labs.

Then, the first rigid tube 12 is rotated relative to the second rigid tube 16 to align the first ring 34 with the second ring 38. This rotating constricts an inner diameter of the elastomeric sleeve 14, which limits mixing of the erythrocyte enriched layer 76 and the plasma enriched layer 74. Preferably this constricting occurs at or very close to the buffy coat, or the boundary between the erythrocyte enriched layer and the plasma enriched layer. Any additional mixing that occurs is preferably negligible to the blood sample analysis. Next, the pin 48 is inserted through both the first and second rings 34/38 to secure a position of the first rigid tube 12 relative to the second rigid tube 16.

In one embodiment, the method further comprises clamping the elastomeric sleeve 14 with a clamp 58 after the rotating. In a further embodiment, this clamping may occur after inserting the pin 48. However, in another embodiment, the pin 48 may be inserted after clamping the blood collection tube 10. The blood collection tube 10 being constricted, holding a separated erythrocyte enriched layer 76 and a separated plasma enriched layer 74, and secured with a pin and/or clamp, is preferably able to maintain the layer separation against inversion, shaking, and other agitation. It is envisioned that because of this structural integrity, the blood collection tube 10 may be used for shipping blood samples easily since the orientation of the tube is not an issue. Similarly, a tube holder or rack is not necessary, ha one embodiment, the method further comprises collecting the plasma enriched layer for analysis or inserting the blood collection tube 10 into a blood analyzing machine. In alternative embodiments, the red blood cell fraction 76 may be collected for analysis if a removable pin or clamp is used, or if the second rigid tube 16 has a valve.

In one embodiment, the method further comprises wrapping a color-changing adhesive tape 72 around the elastomeric sleeve 14 after the rotating. In some embodiments, this wrapping may be done after securing the elastomeric sleeve in a constricted state. The color-changing adhesive tape 72 may be as those embodiments as previously described, and in one embodiment, the color-changing adhesive tape 72 comprises transparent tape with a pH paper 90 on the sticky side.

The invention claimed is:
1. A blood collection tube, comprising:
an elastomeric sleeve having a first end connected to a first rigid tube and a second end connected to a second rigid tube,
the first rigid tube having a penetrable cap removably attached to an end distal to the elastomeric sleeve, and the second rigid tube having a closed end distal to the elastomeric sleeve;

a first ring attached to a first exterior surface of the elastomeric sleeve near the first end;

a second ring attached to a second exterior surface of the elastomeric sleeve near the second end; and a pin configured to insert through both the first and second rings, wherein the first rigid tube, the elastomeric sleeve, and the second rigid tube are configured to confine an evacuated volume, wherein rotating the first rigid tube relative to the second rigid tube decreases a longitudinal length of the elastomeric sleeve and constricts an inner diameter of the elastomeric sleeve, and wherein the constriction severs a fluid communication between the first rigid tube and the second rigid tube.

2. The blood collection tube of claim 1, wherein the elastomeric sleeve is configured to be in a compressed position so that piercing the penetrable cap allows the elastomeric sleeve to expand, thus providing a material transfer of a fluid into the blood collection tube by suction.

3. The blood collection tube of claim 1, wherein the first surface and the second surface are located on substantially opposing exterior surfaces.

4. The blood collection tube of claim 1, wherein the pin comprises a head and a tip, the tip having a barb or a hook.

5. The blood collection tube of claim 1, wherein the pin comprises a plurality of lateral ridges along a longitudinal length, and wherein an interior of the second ring comprises a flexible tab configured to allow movement of the pin in only one direction through the second ring.

6. The blood collection tube of claim 1, wherein the pin comprises screw threads configured to engage with an interior of the first ring and/or the second ring.

7. The blood collection tube of claim 1, wherein the elastomeric sleeve in an uncompressed state has a substantially cylindrical inner diameter.

8. The blood collection tube of claim 1, wherein the elastomeric sleeve in an uncompressed state has a cross-section in a central portion, wherein the cross-section has an aspect ratio in a range of 1.5:1-15:1, and wherein the cross-section is substantially perpendicular to a central axis of the elastomeric sleeve.

9. The blood collection tube of claim 1, wherein the second rigid tube is extendably attached to the elastomeric sleeve so that a distance between the closed end and the second end may be increased or decreased.

10. The blood collection tube of claim 9, further comprising a clamp, wherein the clamp comprises two arms extending from a hinge, each arm terminating with a set of teeth, wherein each set of teeth is configured to engage with the other set of teeth when an area between the two arms is reduced, and wherein the two arms are configured to together pinch the elastomeric sleeve when the elastomeric sleeve is in a constricted position.

11. The blood collection tube of claim 10, wherein each set of teeth is configured to engage with one another irreversibly in one direction.

12. The blood collection tube of claim 10, wherein each arm of the clamp is linear.

13. The blood collection tube of claim 1, wherein the first ring and the second ring are attached near the elastomeric sleeve through a pivotable joint, and wherein the pivotable joint is configured to allow the first ring and the second ring to lie flat against an exterior surface of the blood collection tube.

14. The blood collection tube of claim 1, wherein the first ring and the second ring are attached to a first band and a second band, respectively, and wherein the first band and the second band are each in contact with an exterior circumference of the elastomeric sleeve.

15. The blood collection tube of claim 1, wherein the first rigid tube and the second rigid tube each have a smaller outer diameter in contact with the first end and the second end of the elastomeric sleeve, respectively.

16. The blood collection tube of claim 1, further comprising a color-changing adhesive tape attached to an outside of the first rigid tube, the second rigid tube, and/or the elastomeric sleeve to indicate leaks.

17. A method of using the blood collection tube of claim 1, comprising:

inserting a needle into the penetrable cap, the needle in fluid communication with a volume of blood;

transferring an aliquot of the blood into the blood collection tube by suction;

removing the needle from the penetrable cap;

centrifuging the blood collection tube to produce an erythrocyte enriched layer and a plasma enriched layer from the aliquot of blood;

rotating the first rigid tube relative to the second rigid tube to align the first ring with the second ring, which rotating constricts an inner diameter of the elastomeric sleeve, which constricting limits mixing of the erythrocyte enriched layer and the plasma enriched layer; and inserting the pin through both the first and second rings to secure a position of the first rigid tube relative to the second rigid tube.

18. The method of claim 17, further comprising clamping the elastomeric sleeve with a clamp after the rotating.

19. The method of claim 17, wherein before the inserting, the blood collection tube is in a compressed state.

20. The method of claim 17, wherein during the transferring, the blood collection tube is twisted or squeezed to increase an internal volume.

* * * * *